(12) United States Patent
Esser et al.

(10) Patent No.: US 7,867,761 B2
(45) Date of Patent: Jan. 11, 2011

(54) TRAY STACK ADAPTED FOR ACTIVE GASSING

(75) Inventors: Peter Esser, Copenhagen (DK); Hans Rasmussen, Hvalso (DK); Arne Johansson, St. Laurent de la Salanque (FR)

(73) Assignee: Nunc A/S, Roskilde (DK)

( * ) Notice: Subject to any disclaimer, the term of this patent is extended or adjusted under 35 U.S.C. 154(b) by 1201 days.

(21) Appl. No.: 10/546,478

(22) PCT Filed: Feb. 26, 2004

(86) PCT No.: PCT/DK2004/000127

§ 371 (c)(1), (2), (4) Date: Jul. 7, 2006

(87) PCT Pub. No.: WO2004/076609

PCT Pub. Date: Sep. 10, 2004

(65) Prior Publication Data

US 2007/0065933 A1     Mar. 22, 2007

Related U.S. Application Data

(60) Provisional application No. 60/494,379, filed on Aug. 11, 2003.

(30) Foreign Application Priority Data

Feb. 28, 2003   (DK) ................................ 2003 00321
Sep. 5, 2003    (DK) ................................ 2003 01280

(51) Int. Cl.
    C12M 1/00    (2006.01)
    C12M 3/00    (2006.01)

(52) U.S. Cl. .............. 435/303.1; 435/286.6; 435/305.1; 435/297.1; 435/297.2

(58) Field of Classification Search ... 435/290.1–305.1, 435/303.1, 286.6, 305.2
See application file for complete search history.

(56) References Cited

U.S. PATENT DOCUMENTS

| | | | | |
|---|---|---|---|---|
| 2,865,816 | A | * 12/1958 | Stefanye et al. | ............... 435/39 |
| 3,506,541 | A | *  4/1970 | Snelling | .................... 435/393 |
| 4,172,013 | A | * 10/1979 | Skoda et al. | ................ 435/383 |
| 4,201,845 | A | *  5/1980 | Feder et al. | .............. 435/297.2 |
| 4,786,601 | A |   11/1988 | Rothenberg | |
| 5,010,014 | A |    4/1991 | Gebhardt | |
| 5,955,344 | A | *  9/1999 | Copeland et al. | ............ 435/243 |
| 6,562,616 | B1 | *  5/2003 | Toner et al. | .............. 435/293.1 |
| 6,569,675 | B2 | *  5/2003 | Wall et al. | ................ 435/304.2 |
| 2001/0055803 | A1 | * 12/2001 | Wall et al. | ................ 435/294.1 |
| 2002/0100739 | A1 | *  8/2002 | Day et al. | ................ 211/126.2 |
| 2004/0072347 | A1 | *  4/2004 | Schuler et al. | ............. 435/372 |

FOREIGN PATENT DOCUMENTS

| | | | |
|---|---|---|---|
| CA | 2108055 | * | 10/1994 |
| CA | 2108055 A1 | * | 10/1994 |
| EP | 0 592 936 A1 | | 10/1993 |

\* cited by examiner

*Primary Examiner*—Walter D Griffin
*Assistant Examiner*—Shanta G Doe
(74) *Attorney, Agent, or Firm*—Volentine & Whitt, P.L.L.C.

(57) ABSTRACT

A stack of communicating trays for cultivation of cells, whereby the tray stack is equipped with a gas exchanger having at least one processed aperture for fast and substantially uniform distribution of gas to the trays.

16 Claims, 17 Drawing Sheets

A = Atmosphere above growth medium

AP = Aperture

C = Connecting channel

D = Direction to other connecting channel

G = Gassing direction

GE = Gas exchanger

M = Growth medium above cells

S = Cell substrate of tray

S1 = Cell substrate of above tray

1. Unpack the Cell Factory and place it in a laminar air flow cabinet in order to work in sterile conditions.

2. Prepare cell suspension in an aspirator bottle, mount with sterile connector and clamp.

3. Remove the blue cover cap. Avoid touching the gray port.

4. Immediately insert the connector. Avoid touching the grey port.

6. Gently agitate aspirator bottle. Loosen clamp and cell suspension will flow into the Cell Factory. Chambers will initially fill unevenly but will level when the flow stops.

8. Tilt the Cell Factory towards horizontal position.
*Note: The tilted position is ideal if transporting the filled Cell Factory at any time*

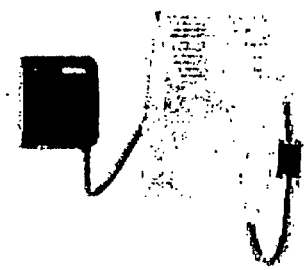

5. Turn Cell Factory on its side with filter upwards and filling port downwards. Raise aspirator bottle above Cell Factory level.

7. After media levelling out, turn the Cell Factory 90 degrees, so that filling port and filter are up. Medium will be separated with equal amounts in each chamber.
*Repeat step 6 and 7 if uneven media distribution.*

Fig. 11B

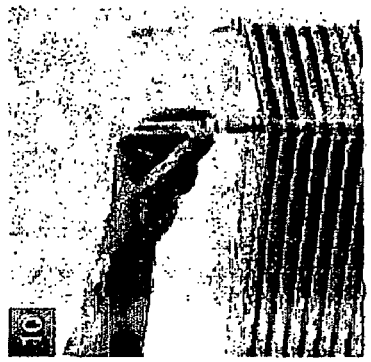

Place the Cell Factory gently in horizontal incubation position. The surface of all the trays will be covered by medium.

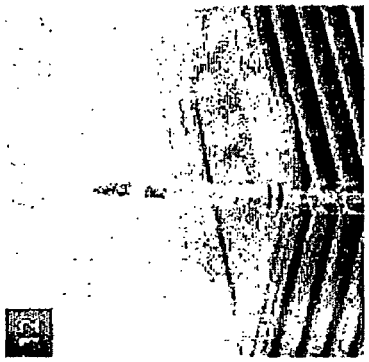

Remove the connector and replace with pre-sterilized connector with filter.

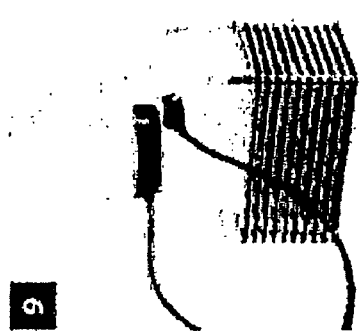

Mount the tubing from gas-exchange-unit to the filter pre-mounted from Nunc.

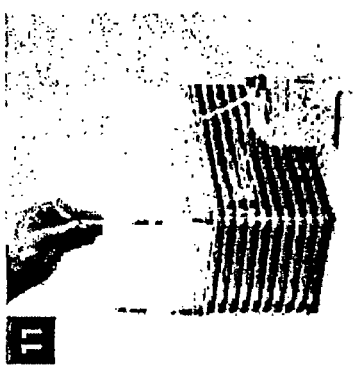

Control your gas supply during incubation. (e.g. continuous or intermittent gassing, gas mix ect.)

Fig. 11C

Tilt the Cell Factory to drain it completely.

A humidifier can be added between pump and Cell Factory if requested.

To empty the Cell Factory place it above aspirator bottle, and the liquid will run out of the Cell Factory.

To decontaminate the Cell Factory after use, it is recommended to autoclave: 60 min. 132 degrees.

TRAY STACK ADAPTED FOR ACTIVE GASSING

CROSS REFERENCE TO RELATED APPLICATIONS

This application claims priority under 35 U.S.C. 119 to Danish application PA 2003 00321 filed on Feb. 28, 2003, and Danish application PA 2003 01280 filed on Sep. 5, 2003, and under 35 U.S.C. 119(e)(1) to U.S. Provisional application Ser. No. 60/494,379 filed on Aug. 11, 2003, which are hereby incorporated by reference.

FIELD OF THE INVENTION

The present invention relates to a stack of communicating trays for the cultivation of cells. The tray stack is equipped with a gas exchanger having at least one processed aperture for fast and substantially uniform distribution of gas to the trays.

BACKGROUND OF THE INVENTION

Cell cultures are used for the production of a vast variety of products, and various methods and apparatus exist for the cultivation of cultures of bacterial and fungal cells, and cells from higher organisms, i.e. eucaryotic cells.

Eucaryotic cells are usable for the generation of a wide range of products, such as virus vaccines, such as, e.g., polio vaccines, cellular chemicals, such as, e.g. interferon and interleukin, immunobiologicals such as, e.g., monoclonal antibodies, and hormones, such as, e.g. insulin.

Eucaryotic cells can be made to grow in two basically different modes. Most eucaryotic cells can be induced to divide only if they are first allowed to attach to a surface or a solid substratum (anchorage dependent), while some can be induced to grow freely in a suspension (anchorage independent).

Nunc™ is producing stacked, communicating tray systems for cell cultivation, called Cell Factories. The Cell Factories can be used for small- or large-scale cultivation of both anchorage dependent and anchorage independent cells. They are suitable for the cultivation of anchorage dependent cells since they provide a large amount of growth surface in a small area with easy handling and low risk of contamination. Due to the simple construction and manageability, the communicating tray system offers an alternative to the substantially more complex and expensive bioreactor or to roller flasks.

However, during the cultivation and production phase the cells will consume oxygen, and produce carbon dioxide, leading to oxygen depletion and acidification of the growth medium. This, in turn, will limit growth and product synthesis. It is found that growth of the cells and cell-based production can be considerably improved if the cells are grown in a constant atmosphere of a defined composition.

Simply supplying gas to the stacked, communicating tray system by entering a defined mixture of gasses has the disadvantage that the individual culture trays are not uniformly provided with oxygen unless a very high flow is applied. Such a high flow may be very difficult to apply due to the fact that the gas must be delivered to the culture trays as sterile gas, i.e. the gas has to be passed through a sterile filter before entering the tray system. The sterile filters will normally not be able to withstand such a high flow, which in practice means that it is not possible to apply such a high flow. Another problem with a high flow rate of gas is that before the gas enters into the tray system the gas must be humidified by passing through a humidifier. Normally, there is an upper limit for the size of the flow through such a humidifier in order to ensure a proper humidification of the gas. If the gas is delivered to the tray system without having been humidified, the medium and/or the cells that are cultivated in the trays will become dehydrated and this, in turn, leads to an unfavourable culturing condition.

EP 0 592 936 describes a method of supplying a defined gas to a stacked, communicating tray system by using a microporous supply line made of a Teflon-type material with pore diameters of between 0.2 µm to 4.0 µm. The pores in the microporous supply line are an inherent feature of the material and the supply line does not have additional processed apertures. When filling or emptying the system with liquid, a bypass valve has to be used, since the microporous system does not have the capacity of rapid pressure equalization, due to the small pore size of the microporous supply line. If the pressure exceeds a certain critical value there it may be detrimental to the system and the system may crack etc.

In EP 0 592 936, it is only illustrated that gas is distributed to the first tray in a stacked, communication tray device. In other words, EP 0 592 936 does not disclose whether gas distribution through a microporous supply line gives a fast and uniform distribution of gas to all trays in a device.

SUMMARY OF THE INVENTION

Thus, there is a need for a way to distribute a gas fast and uniformly to a stacked, communicating tray system, and wherein liquid may be supplied to or drained from the device at a fast flow rate.

According to a first aspect of the invention, the above-mentioned and other objects are fulfilled by a tray stack for cultivation of cells, comprising a plurality of trays and a first connecting channel, each tray having an opening through which the tray communicates with the first connecting channel, the channel having a gas exchanger having at least one processed aperture for fast and substantially uniform distribution of gas to the trays.

According to a second aspect of the invention, the above-mentioned and other objects are fulfilled by a method for cultivating cells in stacked communicating trays, the method comprising applying a suspension of cells into the tray stack, and incubating the tray stack containing the suspension of cells under suitable conditions.

According to a third aspect of the invention, the above-mentioned and other objects are fulfilled by a gas exchanger for use in the tray stack.

DEFINITIONS

Throughout the text including the claims, the following terms shall be defined as indicated below.

By the term "tray stack" is intended to mean a plurality of trays that are positioned on top of each other when the trays are in a horizontal position.

By the term "aperture" is intended to mean an opening having any suitable shape, such as circular, rectangular, square, polygonal etc.

By the term "processed aperture" is intended to mean an aperture, which has been made in the gas exchanger material. In other words, the aperture is not an inherent feature of the gas exchanger material.

The term "an axis of aperture" intends to describe an axis passing through the aperture and extending perpendicular to the plane of the aperture.

The term "diameter" is a characteristic dimension of the aperture and in the present context it embraces e.g. a diameter of a circle, a length of a slot, the longest side of a polygon etc.

In the present context the term "exchange of gas" is intended to denote that at least about 30% of the gas present in the headspace is exchanged with gas from an external supply. Normally at least about 40% such as, e.g., at least about 50 or at least about 60% is exchanged.

By the term "head-space" is intended to mean the gas-filled space above the liquid in the trays.

The tray stack according to the invention may have any suitable shape, such as, e.g., rectangular, square, round, circular, oblong, elliptical, polygonal or trapezoidal. Normally the trays are connected through two separate first and second connecting channels, the second channel being used for supply of liquid to the trays and the first channel being used for transport of the air out of the trays when the liquid Is filled into the trays to avoid a pressure rise (see FIG. 1). The first and second connecting channels may be designed in any suitable form and may be placed at any suitable site of the tray stack. With respect to the present invention, the first connecting channel has a gas exchanger, which is used to further supply gas to the trays in order to enable improved conditions for cultivation of cells.

The gas exchanger and/or the tray stack may be made of a material that withstands sterilization, such as, e.g., sterilization by irradiation (beta or gamma radiation), steam autoclave, ethylene oxide, chemical disinfectants, or dry heat sterilization.

In an embodiment of the invention, the gas exchanger and/or the tray stack are made from a thermoplastic material and/or from a material that is processable by extrusion. Examples of materials that are suitable for use in the present context are e.g., polyethylene, polypropylene, polystyrene, polycarbonate, polyurethane, polysulfone, polymethylpentene, polymethylmetacrylate, polyethyleneterepthtalate, polytetrafluoroethylene, or ABS (acrylonitrilbutadiene styrene). However, the examples given here only illustrate suitable materials and a person skilled in the art will know how to select other materials suitable for use as a gas exchanger material.

In a further embodiment, the gas exchanger and/or the tray stack are made of a material that withstands radiation such as, e.g., gamma radiation. The gas exchanger may then be placed in the stacked, communicating tray device according to the invention before sterilization, and the whole device may be sterilized together, greatly decreasing the risk of contamination. The gas exchanger may be made of any suitable material, which is capable of withstanding radiation, such as, e.g., a thermoplastic material.

In another embodiment of the invention the gas exchanger may be made of stainless steel.

The gas exchanger may be moulded together with the stacked, communicating trays in the tray stack or it may be placed in the tray stack in a separate step.

When working with potentially hazardous cells or cell products, it may be desired to autoclave the whole device after use. In other words, it may be desirable to use a tray stack made of a material that melts by autoclaving. In that specific situation, it is preferred that the device is equipped with a gas exchanger made from a material with the same or a lower melting temperature than the rest of the device.

The gas exchanger may form part of or constitute the first connecting channel (i.e. being processed together with the tray stack) or it may be inserted into the first connecting channel at a later stage of the processing of the tray stack.

The gas exchanger is constructed in such a manner that it is possible to prevent a critical pressure rise in the tray stack when the tray stack is supplied with or drained of a liquid. Furthermore, it allows for supplying the trays of the tray stack with a gas from an external supply. Accordingly, the gas exchanger has at least one aperture. The at least one aperture is a processed aperture, i.e. it is not an inherent feature of the gas exchanger material. The processed aperture may have any suitable form (such as, e.g., circular, round, elliptical, oblong, polygonal, rectangular, square, trapezoidal etc) and it may have any suitable size. The number of apertures may vary over a wide range. Thus, in some embodiments, there is one aperture per tray (see FIG. 2), and in other embodiments there is a set of apertures (i.e. two or more apertures) per tray (see e.g. FIG. 7 herein). In other embodiments, there is only one aperture (or set of apertures) per every second, third etc. trays, and in a still further embodiment, there is only one aperture or set of apertures. The specific embodiments mentioned herein should not in any way limit the invention, once a person skilled in the art has understood the idea behind the invention it is possible to construct gas exchangers having other positions and sizes of the apertures and such gas exchangers are also within the scope of the present invention.

In one embodiment of the invention the gas exchanger has a plurality of apertures or set of apertures. The apertures or set of apertures may equal the number of trays, such as, e.g. 1, 2, 3, 4, 5, 10, 15, 20, 25, 30, 35, 40, 45, 50 or more apertures or set of apertures. This is e.g. the case, when the first connecting channel constitutes the gas exchanger.

The number of apertures or set of apertures of the gas exchanger may be larger than, equal to or smaller than the number of trays. In one embodiment, there may be one or more apertures or set of apertures per tray, such as, e.g. at least 2, at least 3, at least 4, at least 5 or at least 10 as long as the total area of the apertures allows for a uniformly and fast distribution of gas through the tray stack. In yet another embodiment the gas exchanger has only 1 aperture or set of apertures per $2^{nd}$ tray, per $3^{rd}$ tray, per $4^{th}$ tray, per $5^{th}$ tray or per $6^{th}$ tray or more. Other variations are also within the scope of the present invention.

In a further embodiment of the invention an axis of the aperture extends along a longitudinal direction of the respective tray.

The term "longitudinal" relates to a tray stack wherein the trays have a rectangular shape, but the trays may have any suitable shape, such as, e.g., rectangular, square, round, circular, oblong, elliptical, polygonal or trapezoidal. Therefore, the expression "longitudinal extension" is intended to mean that the gas is introduced into the tray along that part of the tray that causes the gas to travel the longest path before leaving through the second connecting channel.

The invention relates to a tray stack wherein the aperture has an area that leads to the creation of a relatively fast moving gas flow into the respective tray. The aperture may have the same effect as a nozzle, creating a relatively fast moving gas flow.

In a specific embodiment, the gas exchanger may have one aperture positioned in the lower part of the first connecting channel, when the device is positioned in its operating position. The gas exchanger may be a tube with the aperture at one end and connected to a gas supply at the other end. The aperture may be circular and have a diameter of 1 mm or more such as, e.g., 2 mm or more, 3 mm or more, 5 mm or more, 8 mm or more etc. As discussed herein, the aperture may have any form and it may also be in the form of e.g. a slot.

By the term "lower part" is intended to mean the lower half part of the channel, when the device is positioned in its upright operating position for cultivating cells. For example, the gas exchanger may have one aperture positioned at the bottom of the first connecting channel. Furthermore, an axis of the aperture may extend towards the bottom of the channel. This embodiment is suitable for use especially in tray stacks having about 40 trays or less such as, e.g., about 35 trays or less, about 30 trays or less, about 25 trays or less, about 20 trays or less, about 15 trays or less or about 10 trays or less.

Normally, a tray stack according to the invention has more than one tray such as, e.g., at least 5 trays, at least 10 trays, at least 11, at least 12, at least 13, at least 14, at least 15, at least 20, at least 25, at least 30, at least 35, at least 40, at least 45 or at least 50 trays.

As mentioned above, in certain cases it is an advantage to use a limited number of trays and then the tray stack contains at the most 20 trays, such as, e.g. at the most 19, at the most 18, at the most 17, at the most 16, at the most 15, at the most 14, at the most 13, at the most 12, at the most 11, at the most 10, at the most 9, at the most 8, at the most 7, at the most 6, at the most 5, at the most 4, at the most 3, or at the most 2 trays.

The aperture(s) of the gas exchanger prevents a critical pressure rise and allows for fast pressure equalization when the device is supplied with or drained of a liquid. As compared to a microporous system the size of the aperture(s) of the gas exchanger of the present invention allows for a relatively fast gas output when supplying liquid to the system, and a relatively fast gas intake when draining the system of liquid.

The aperture(s) may be placed at any suitable position of the gas exchanger. Thus, the aperture(s) may be placed in front of the respective openings of the trays, they may be displaced from the openings or the aperture may be positioned opposite to the respective tray openings. Moreover, the centre axis of the aperture may extend into the respective tray opening in a specific angel to the tray sides In a specific embodiment the at least one aperture is positioned in front of the respective openings of the trays and/or an axis of the at least one aperture extends along a longitudinal direction of the respective tray.

Normally, the at least one aperture of a tray stack according to the invention has a diameter of at the most about 2.0 mm such as, e.g., at the most about 1.8 mm, at the most about 1.6 mm, at the most about 1.5 mm, at the most about 1.4 mm, at the most about 1.2 mm, at the most about 1.0 mm, at the most about 0.9 mm, at the most about 0.8 mm, at the most about 0.7 mm, at the most about 0.6 mm, or less about 0.5 mm.

Due to the fact that the aperture(s) may have any suitable shape (round, circular, elliptical, oblong, polygonal etc.) another measure for the size of the aperture is the area of the aperture. Normally, the at least one aperture has an area of at the most about 3.5 mm$^2$ such as, e.g., at the most about 3.2 mm$^2$, at the most about 3.0 mm$^2$, at the most about 2.8 mm$^2$, at the most about 2.5 mm$^2$, at the most about 2.3 mm$^2$, at the most about 2.0 mm$^2$, at the most about 1.8 mm$^2$, at the most about 1.6 mm$^2$, at the most about 1.4 mm$^2$, at the most about 1.2 mm$^2$, at the most about 1.0 mm$^2$, at the most about 0.8 mm$^2$ or at the most about 0.6 mm$^2$.

Gas may be supplied to the gas exchanger from an external gas supply. The gas used may be atmospheric air, or any defined gas or mixture of gasses with a suitable composition for cultivation of the respective cells. In one embodiment of the invention, the gas is comprised of defined amounts of $O_2$, $CO_2$ and $N_2$.

The gas is distributed to the headspace in the trays, thereby being in direct contact with the liquid in the trays, and the gas has to be transferred across the boundary between the gas phase and the liquid phase. In principle, the driving force is the difference between the gas concentration in the liquid at the interface and the concentration in the bulk of the liquid, and the gas is diffusing from the headspace in the trays to the liquid. At constant temperature and pressure the concentration of gasses in the medium in equilibrium with the headspace is proportional to the partial pressure of the various gasses in the gas phase.

In principle any suitable flow of gas can be employed, but in those cases—which are relevant when culturing cells or cell-based products—where the gas has to be humidified and/or sterilized before entering into the tray stack, the flow must be lower a certain critical value. Therefore, in a tray stack according to the present invention, the flow rate of gas per tray is normally at the most about 500 ml/min per tray such as, e.g., at the most about 400 ml/min, at the most about 300 ml/min, at the most about 250 ml/min or at the most about 200 ml/min.

Satisfactory results may also be obtained by employing a tray stack according to the present invention, wherein the flow rate or gas per tray is at the most about 100 ml/min such as at the most about 90 ml/min, at the most about 85 ml/min, at the most about 80 ml/min, at the most about 75 ml/min, at the most about 70 ml/min, at the most about 65 ml/min, at the most about 60 ml/min, at the most about 55 m/min or at the most about 50 ml/min.

In a very specific embodiment the tray stack according to the invention is supplied with a gas that has a flow rate of gas per tray is 50 ml/min, and the at least one aperture has a diameter of 0.4 mm.

As mentioned above, the gas is delivered to the tray stack in order to exchange the gas contained in the headspace to such an extent that the culturing conditions for the cells contained in the trays are as desired. The gas supply may be delivered continuously to the device or it may be delivered in pulses during certain ventilation time periods at certain time intervals. Normally, it is not necessary to deliver the gas continuously and it is e.g. delivered during a ventilation time period of at the most about 1 h, such as at the most about 0.75 h, at the most about 0.5 h, at the most about 0.25 h, and or the most about 0.10 hours. The specific conditions depend on the cells cultured, the medium, and the size of the headspace, the flow, the design of the gas exchanger etc.

The gas may be delivered in pulses with duration and a flow rate that provides for the exchange of at least 50% of the headspace gas in a specified time period. In one embodiment the gas may be delivered e.g. at time intervals of every 3 or 2 hours at a flow rate of e.g. 50 ml/min per tray during a ventilation time period of, e.g., 15 minutes.

By choosing a suitable number and areas of apertures together with a corresponding flow rate, a backpressure is normally established in some of the embodiments of the invention, allowing the gas to be distributed evenly in the gas exchanger and hence in the trays.

In specific embodiments the invention relates to a tray stack, wherein the flow rate of gas per tray during a time period for ventilation of the headspace of the individual trays is 50 ml/min, and the at least one aperture has a diameter of 0.4 mm and/or the gas exchanger may be a tube having an aperture for each tray, the apertures being placed at a distance of about 17 mm to each other.

It is an advantage of the invention that the gas flow provided by the gas exchanger does not only exchange gas in the headspace above the liquid in the trays, but also effects stirring of the liquid thereby further enhancing supply of oxygen to the cells in the liquid.

In one embodiment of the invention, the stirring effect may be further utilized by increasing the gas flow rate during a short time period to effect further stirring of the liquid. Thus, during a stirring time period that is typically shorter than the ventilation time period, the flow rate of gas is at least larger, such as 5 times larger, preferably app. 10 times larger, etc., than the flow rate during the ventilation time period whereby liquid in each of the trays is stirred.

The tray stack may further comprise a sterile filter at the input to the first connecting channel, and a branched manifold with a sterile filter at the input/output of second connecting channel, the manifold facilitating communication with the trays, such as adding medium, subtracting a sample, etc, without any manipulation of the sterile filters.

Details and particulars relating to the above-mentioned aspect of the invention (tray stack) apply mutatis mutandis to the other aspects of the invention (gas exchanger, method for cultivating cells etc.)

DESCRIPTION OF PREFERRED EMBODIMENTS

Figure 1:
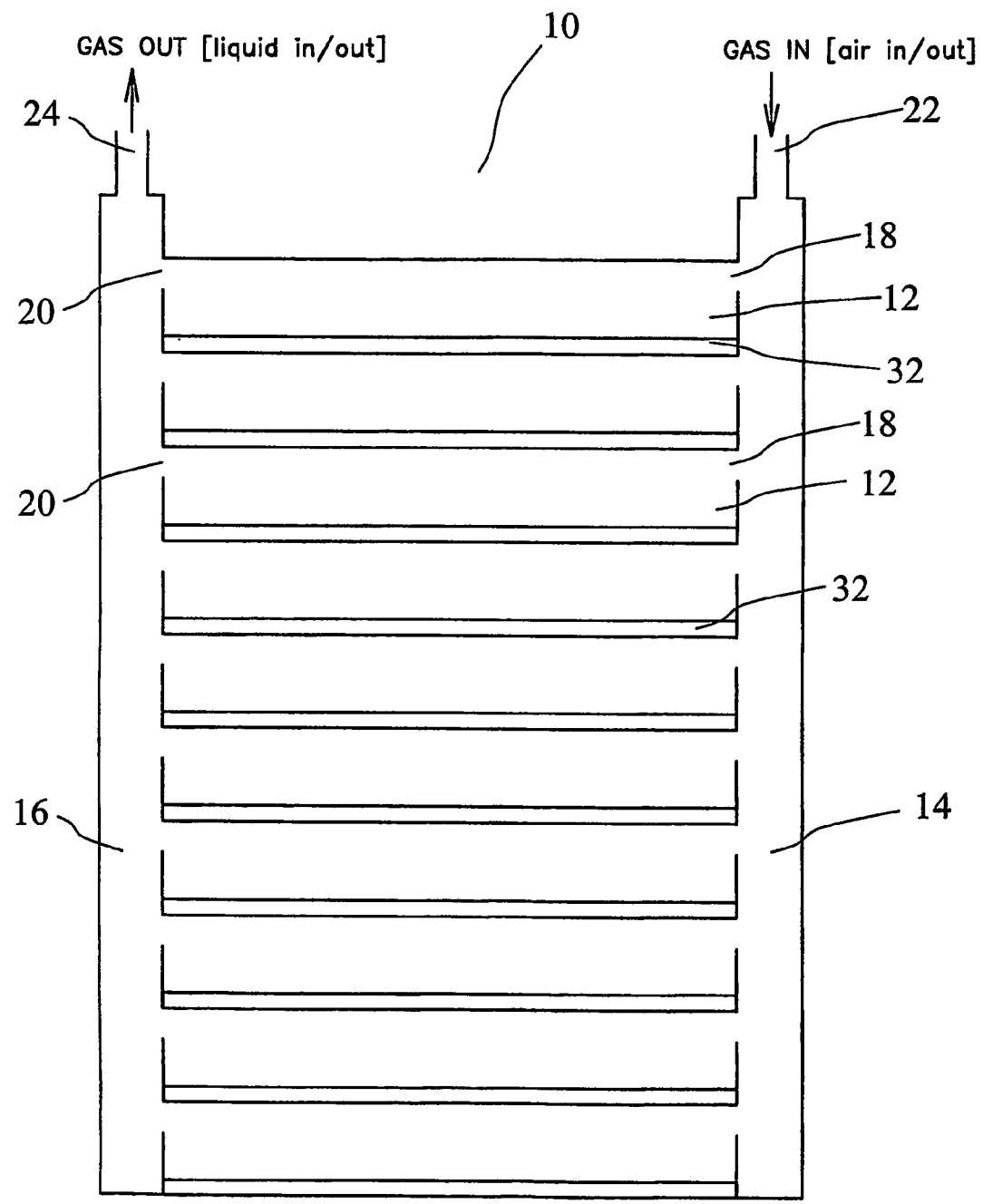
FIG. 1 schematically illustrates a prior art communicating tray stack.

FIG. 1 schematically illustrates a prior art tray stack 10 for cultivation of cells, comprising a plurality of trays 12 and a first connecting channel 14 and a second connecting channel 16. Each tray 12 has an opening 18 through which the tray 12 communicates with the first connecting channel 14 for exchange of air between the channel 14 and the respective tray 12. Similarly, each tray 12 has an opening 20 through which the tray 12 communicates with the second connecting channel 16 for exchange of air or liquid between the second channel 16 and the respective tray 12. Air may be input to or output from the first connecting channel 14 through a first port 22, and air or liquid may be input to or output from the second connecting channel 16 through a second port 24.

The second connecting channel 16 is used for supplying or draining liquid from the tray stack 10 and for escape of gas during cultivation and when gas is added to the tray stack 10 through the first port 22.

During cultivation of cells and cell-based production in the illustrated prior art tray stack 10, the cells consume oxygen and produce carbon dioxide. This leads to oxygen depletion and acidification of the growth medium. This, in turn, will limit growth and product synthesis. It has been found that growth of the cells and cell-based production can be considerably improved if the cells are grown in a constant atmosphere of a defined composition.

As described in more detail in the introduction, simply supplying gas to the stacked, communicating tray system 10 by entering a defined mixture of gasses through the first port 22—and without employing a relatively high flow—has the disadvantage that the individual culture trays 12 are not uniformly provided with oxygen, leading to an uneven growth of cells and reduced yields. Furthermore, the gas needs to be entered at a very high flow rate, which renders it a very expensive method based on the poor outcome.

Figure 2:
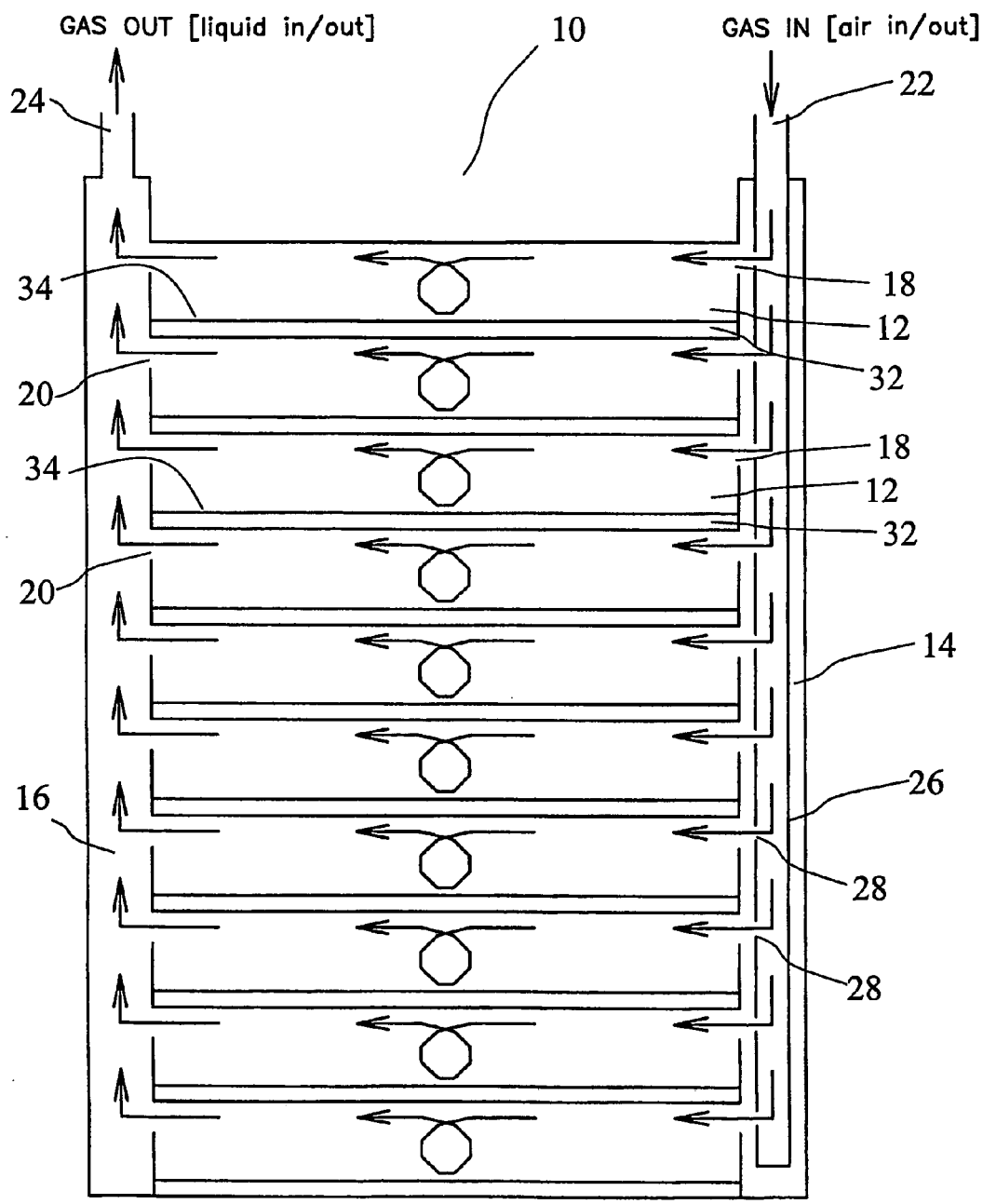
FIG. 2 schematically illustrates an embodiment of the invention.

FIG. 2 schematically illustrates a tray stack 10 according to the present invention for cultivation of cells, comprising a plurality of trays 12 and a first and a second connecting channel 14, 16. Each tray 12 has an opening 18 through which the tray 12 communicates with the first connecting channel 14 for exchange of air between the first connecting channel 14 and the respective tray 12. Similarly, each tray 12 has an opening 20 through which the tray 12 communicates with the second connecting channel 16 for exchange of air or liquid between the second channel 16 and the respective tray 12. Air may be input to or output from the first connecting channel 14 through a first port 22, and air or liquid may be input to or output from the second connecting channel 16 through a second port 24.

Figure 2A:
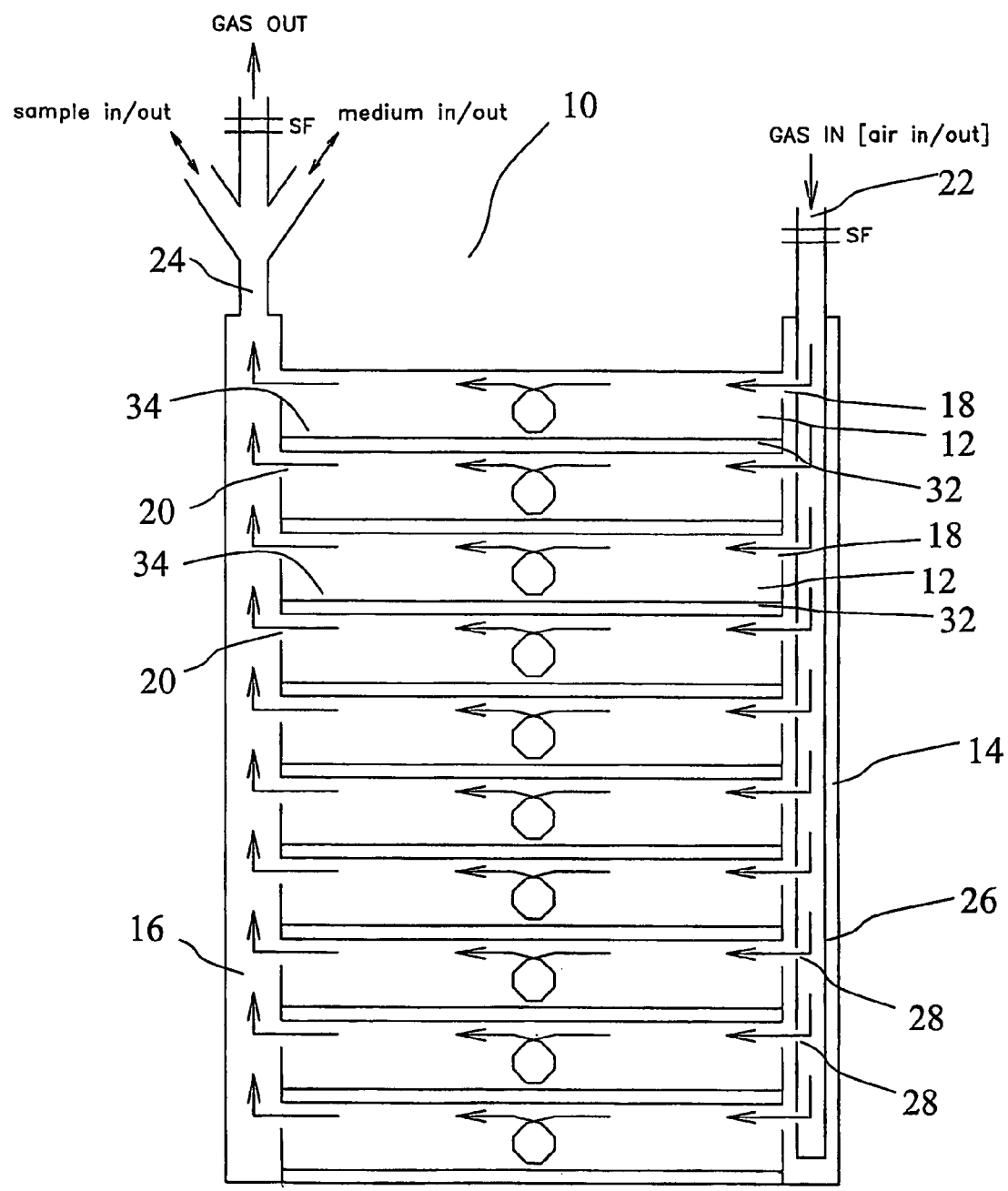
FIG. 2A schematically illustrates the embodiment of FIG. 2 with a manifold.

The tray stack 10 of FIG. 2A further comprises a gas exchanger 26 having at least one processed aperture 28 for fast and substantially uniform distribution of gas to the trays 12. In the illustrated embodiment 10, the gas exchanger 26 has one aperture 28 per tray 12, and each 28 of the at least one aperture is placed in front of the tray opening, i.e. an axis of the aperture 28 and an axis of the respective opening 18 substantially coincide whereby a very fast and efficient gas distribution is provided.

The apertures 28 of the gas exchanger 26 and the flow rate of gas into the first port 22 cooperate to provide a substantially uniform distribution of gas 30 among the trays 12. Further, the gas 30 is distributed substantially across the entire surface of the liquid 32 in the trays, and the gas 30 is also transferred across the boundary 34 between the gas phase 36 and the liquid phase 32. In principle, the driving force is the difference between the gas concentration in the liquid at the interface 34 and the concentration in the bulk of the liquid 32, and the gas 30 is diffusing from the headspace 36 in the trays 12 to the liquid 32. At constant temperature and pressure the concentration of gasses in the medium 32 in equilibrium with the headspace 36 is proportional to the partial pressure of the various gasses in the gas phase.

FIG. 2A schematically illustrates the embodiment of FIG. 2 with a manifold positioned at the second port 24.

Figure 2B:
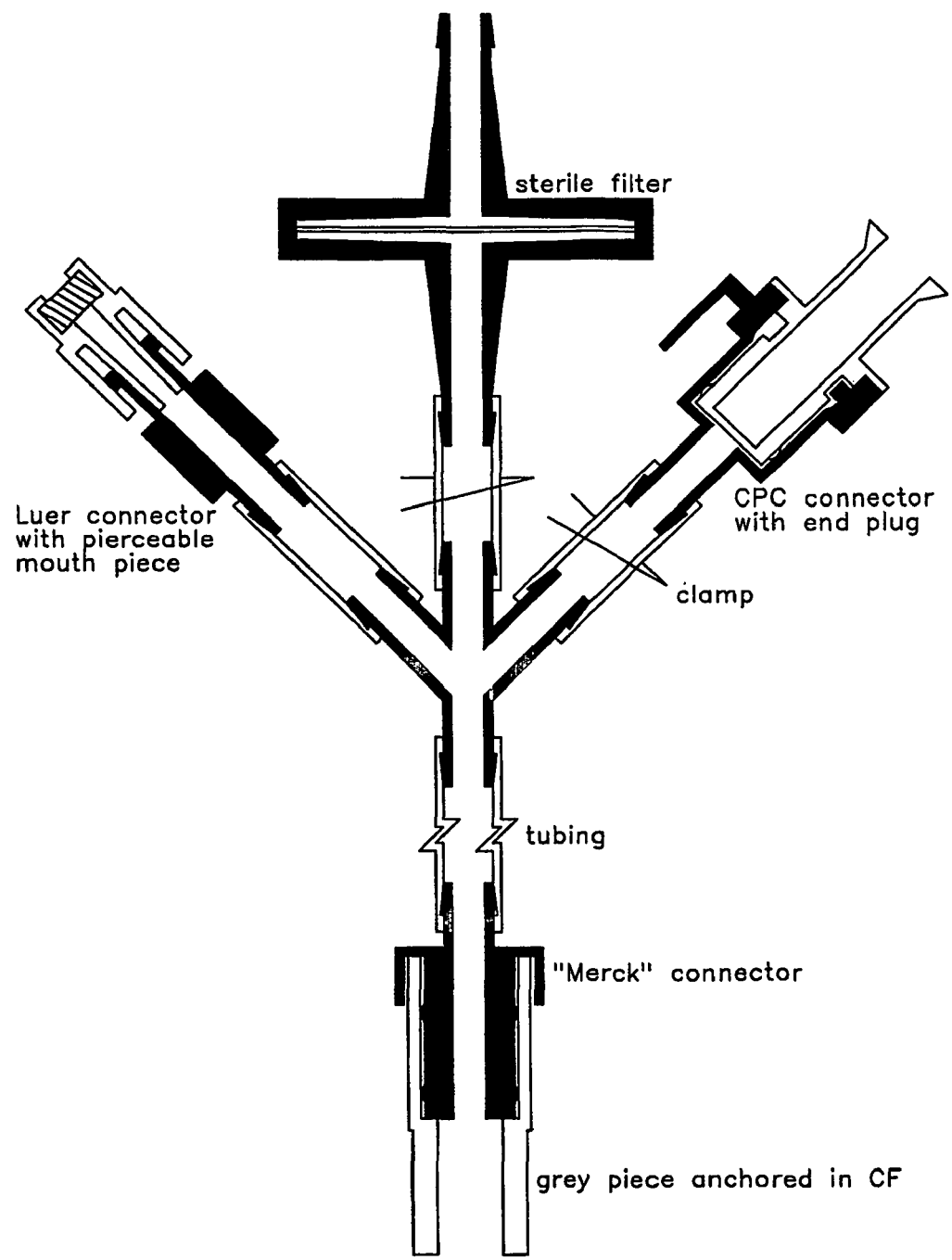
FIG. 2B schematically illustrates a manifold according to the invention.

FIG. 2B schematically illustrates the branched manifold positioned at the second port 24 in further detail. The first port 22 and the second port 24 are further provided with a sterile filter SF. Such an embodiment allows for additional input or output of e.g. media (addition of further medium and/or removal of medium or substitution of medium), sampling or addition of further material without any manipulation of the sterile filter. Thus, the risk for microbial contamination is reduced.

Figure 3:
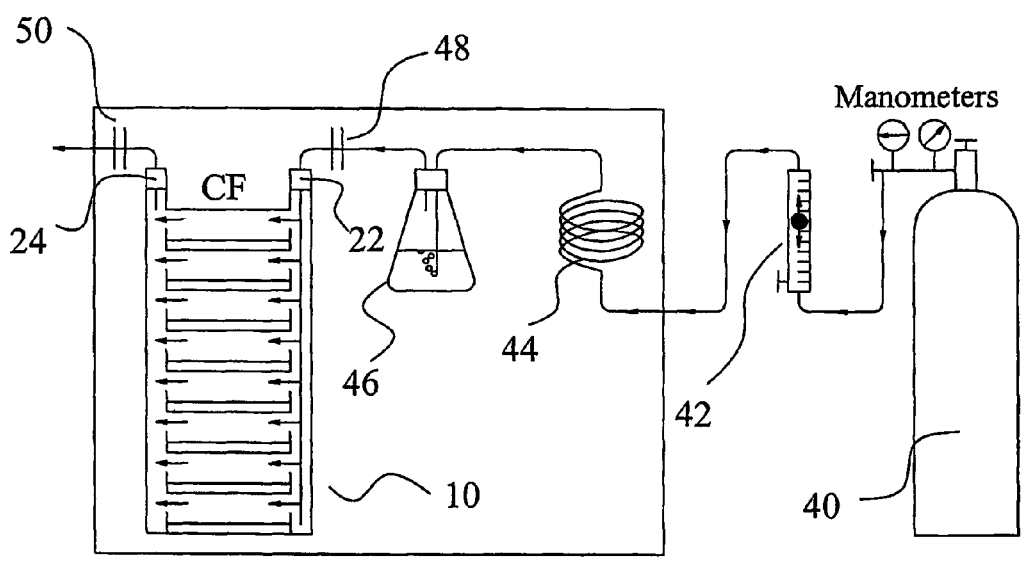
FIG. 3 schematically illustrates a first embodiment of the invention connected to a gas supply, FIG. 4 schematically illustrates a second embodiment of the invention, FIG. 5 schematically illustrates a third embodiment of the invention, FIG. 6 schematically illustrates a fourth embodiment of the invention.

FIG. 3 schematically illustrates a set-up for supplying gas to a tray stack 10 according to the present invention during cell cultivation. The set-up comprises a source of pressurized air 40 connected to the tray stack via a flow meter 42, a heater 44, a humidifier 46 and a sterile filter 48 and the first port 22. Another sterile filter 50 is connected to the second port 24. It is important to note that the sterile filters 48, 50 as well as the humidifier 46 limit the obtainable maximum flow rate, and it is an important advantage of the present invention that the tray apertures 28 of the gas exchanger 26 can be designed to co-operate with the input gas flow rate to obtain a fast and uniform distribution of gas among the trays 12 while maintaining the input gas flow rate below the limit allowed by the sterile filters 48, 50, e.g. a flow rate below 250 ml/min per tray.

Figure 4:
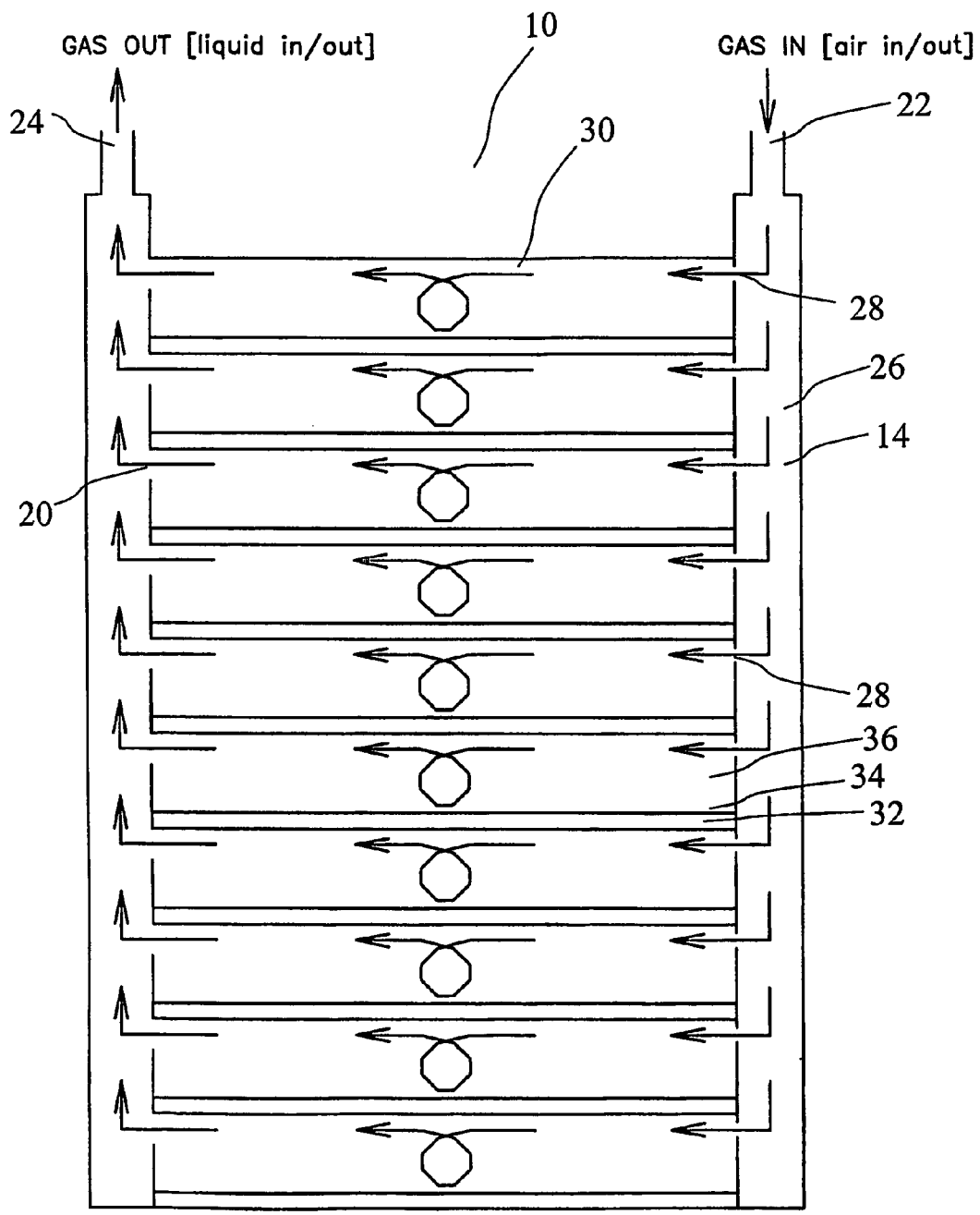

FIG. 4 schematically illustrates an embodiment of the invention wherein the gas exchanger 26 is constituted by the first connecting channel 14. The gas exchanger 26 has one aperture 28 per tray 12.

Figure 5:
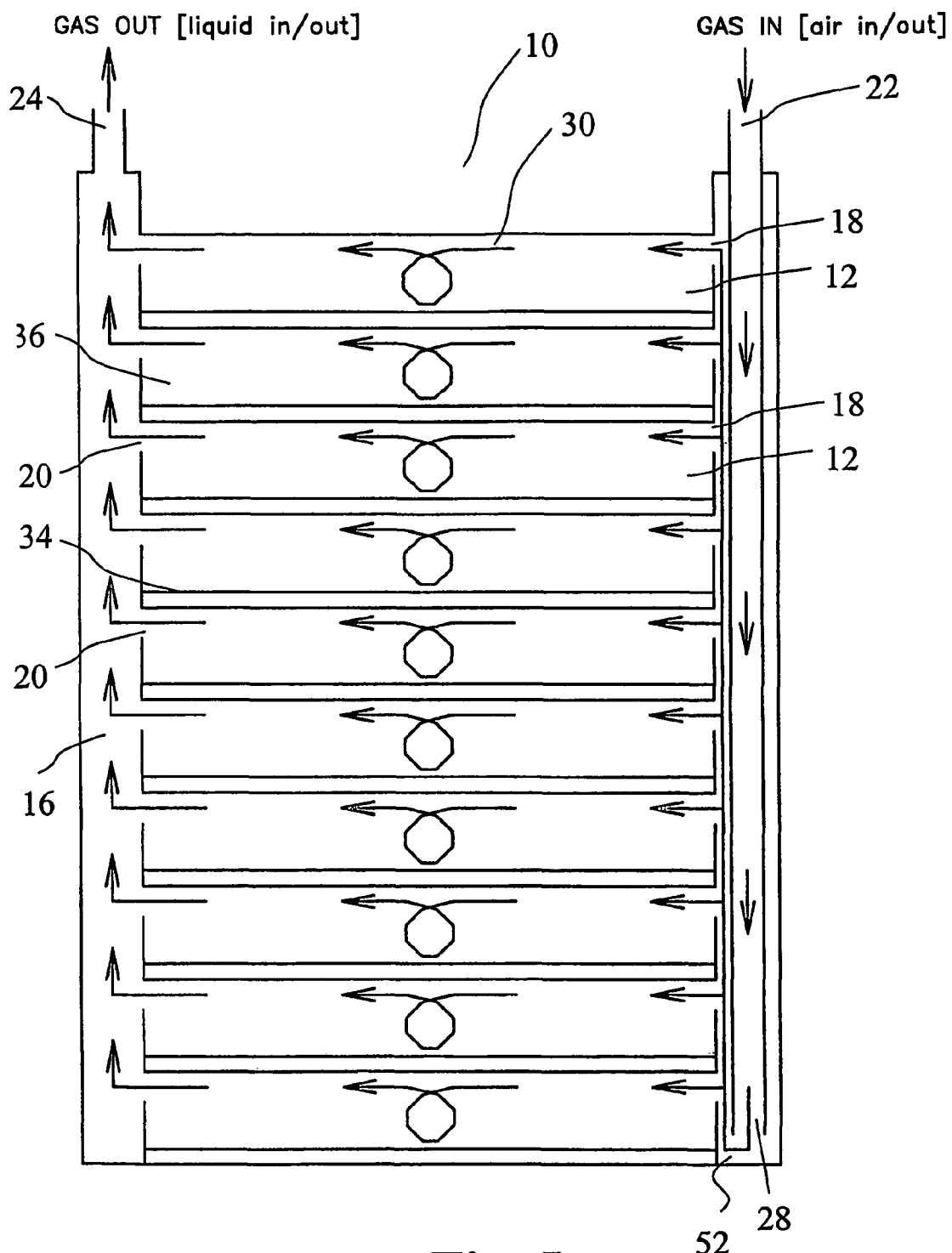

FIG. 5 schematically illustrates an embodiment of the invention wherein the gas exchanger 26 is a tube with one aperture 28 in the end of the tube facing towards the bottom 52 of the first connecting channel 14.

Figure 6:
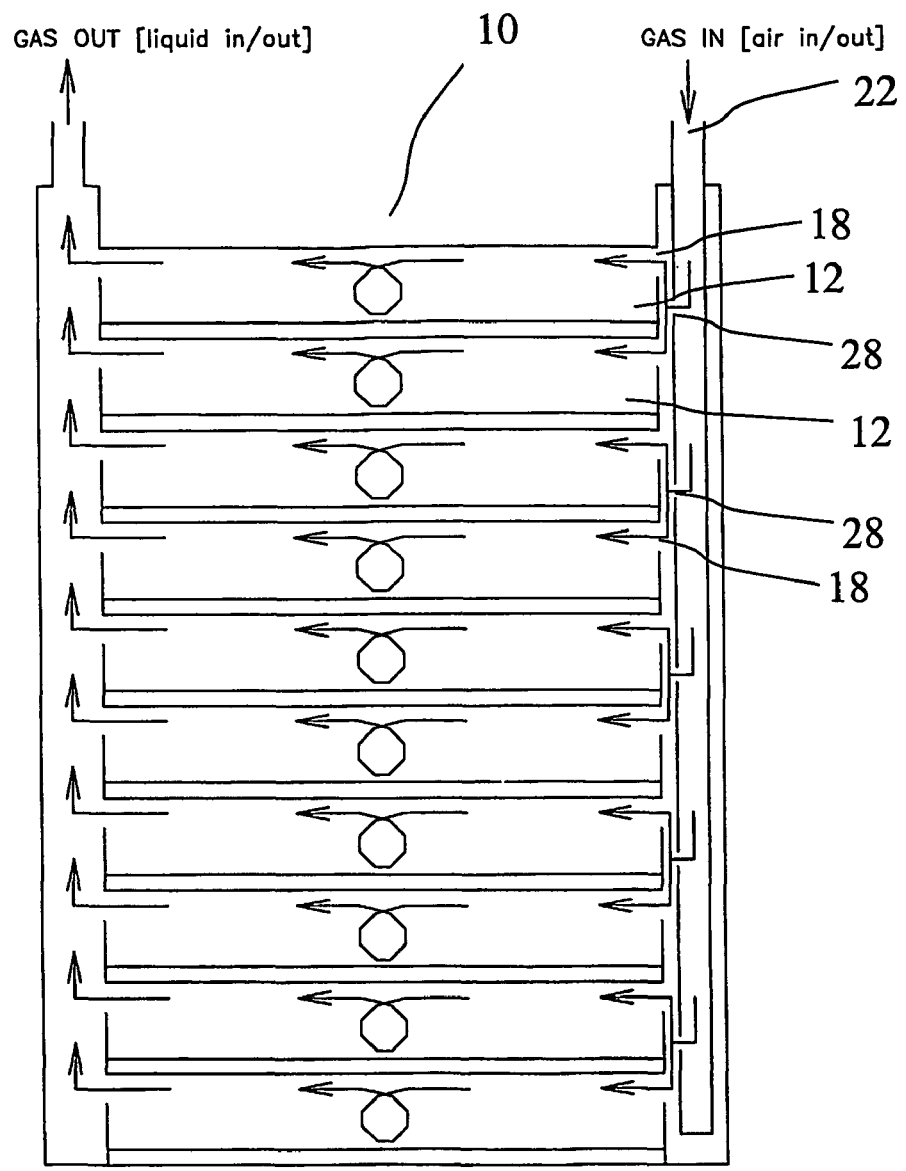

FIG. 6 schematically illustrates an embodiment of the invention wherein the gas exchanger 26 is a tube with one aperture 28 per every second tray 12. Other embodiments may have one aperture per every $3^{rd}$ tray, per every $4^{th}$ tray, per every $5^{th}$ tray or per every $6^{th}$ tray.

Figure 7:
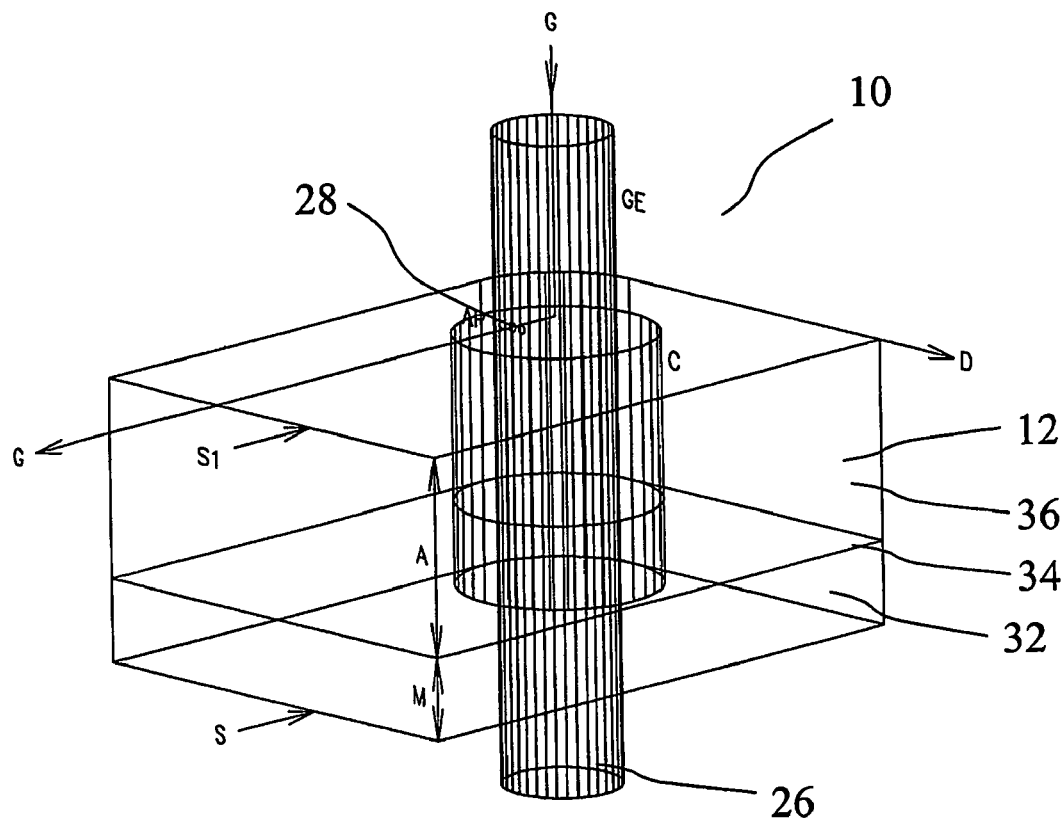
FIG. 7 is a perspective view of a part of an embodiment of the invention, FIG. 8 are plots of the oxygen content of every third of the trays for various embodiments and conditions, FIG. 9 are plots of the oxygen content of every third of the trays for various embodiments and conditions.

FIG. 7 is a perspective 3-dimensional view of a part of a tray stack 10 according to the invention. The illustrated embodiment has three apertures 28 per tray 12, and the positioning of the apertures 28 is in the upper part of the respective tray 12 allowing gas from an external supply to be delivery in a direction G that is perpendicular to the direction D towards the second connection channel 16 (not shown). An axis of each aperture 28 is extending into the respective tray opening 18 along the direction G. In another embodiment, the gas exchanger has at least one apertures per tray opening, such as, e.g., at least 2, at least 3, at least 4, at least 5 or at least 6.

Figure 8A:
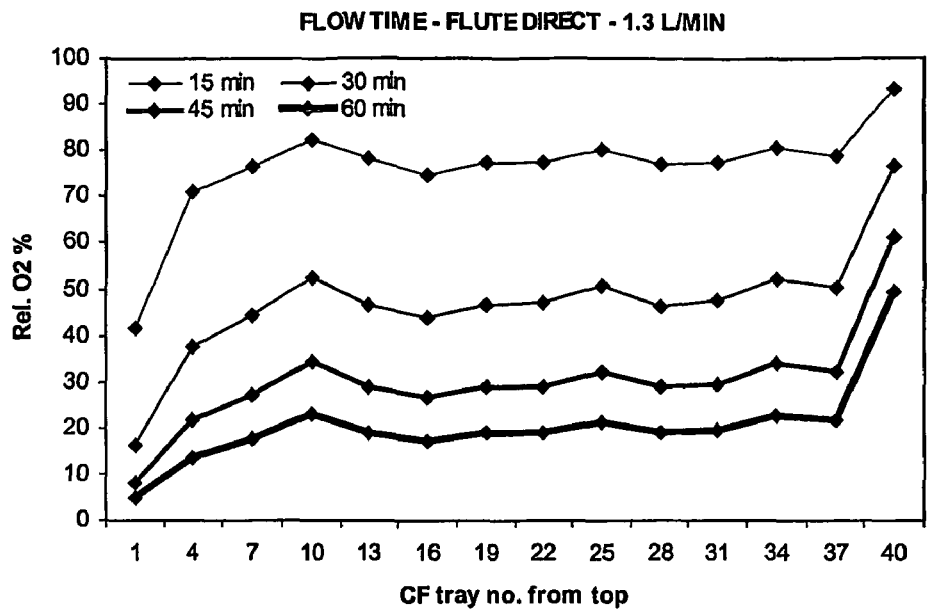
Figure 8B:
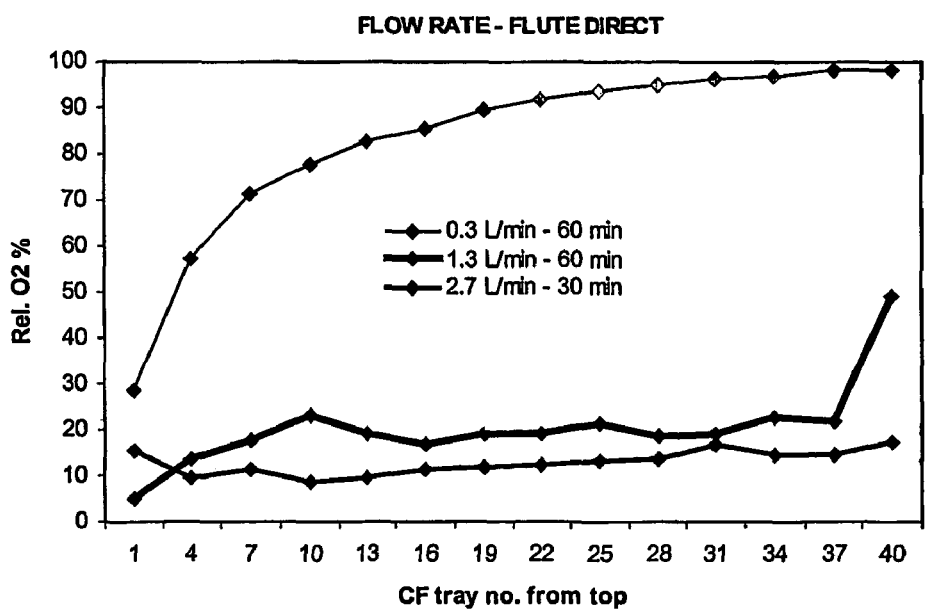
Figure 8C:
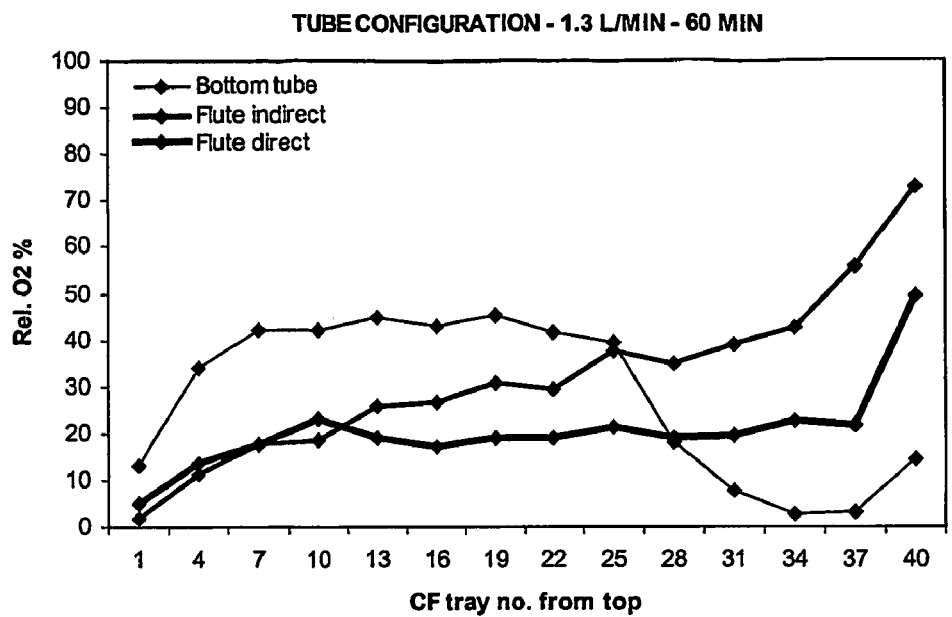

FIG. 8A illustrates the time for distribution of a gas. FIG. 8B illustrates the gas distribution at different flow rates of gas. FIG. 8C illustrates the distribution of gas when using different gas exchanger designs.

Figure 9A:
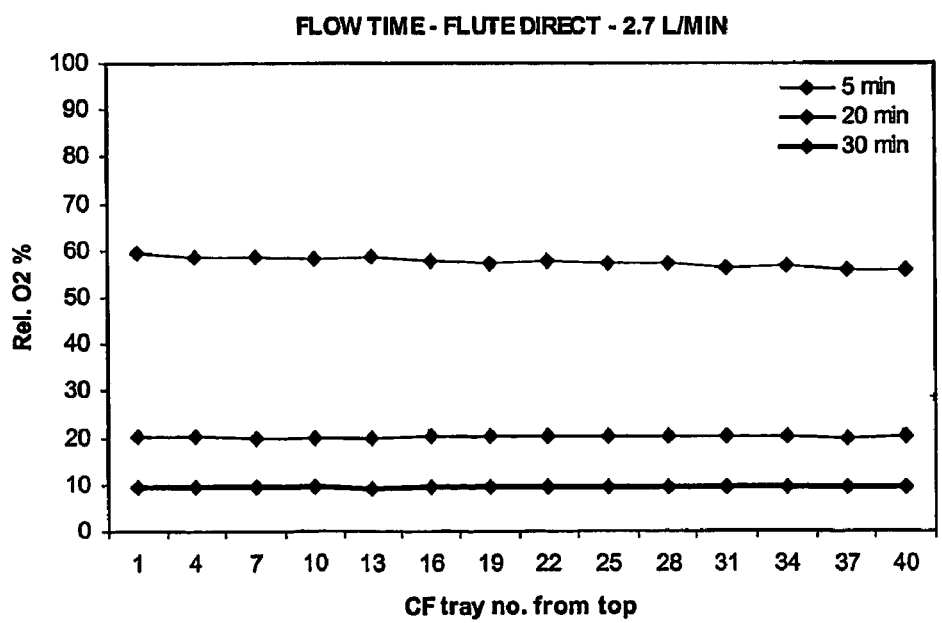
Figure 9B:
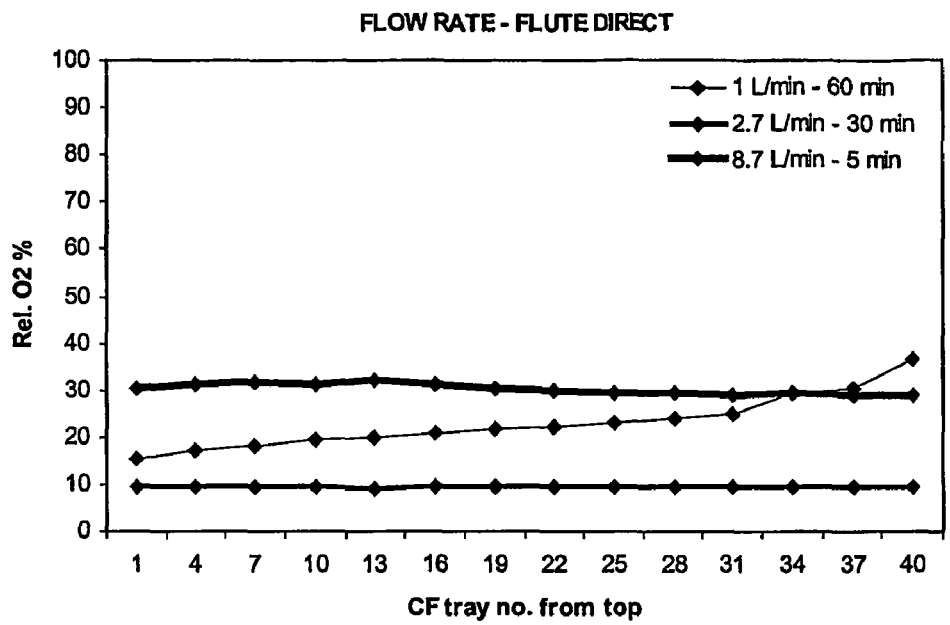
Figure 9C:
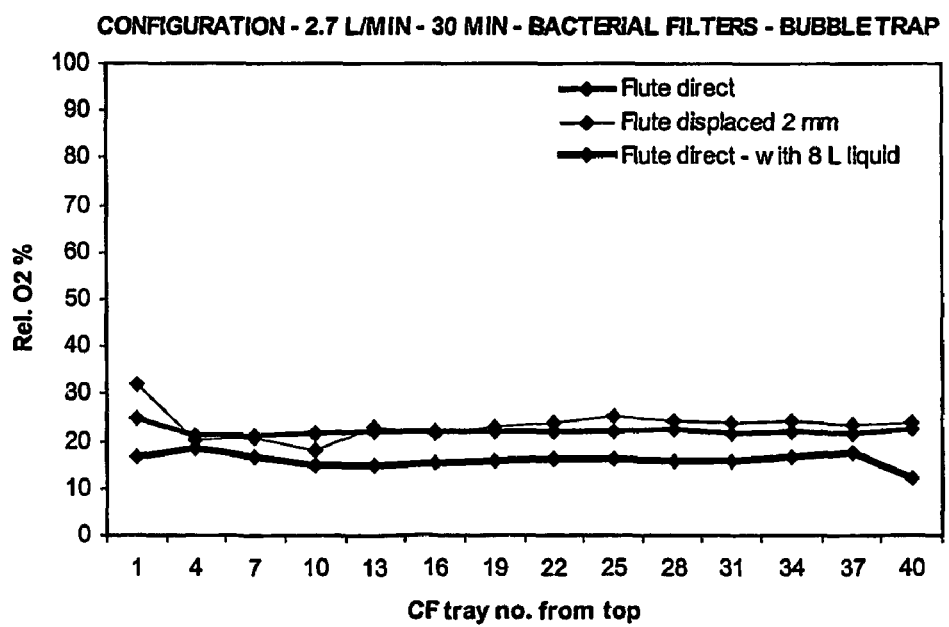

FIG. 9A illustrates the time for distribution of a gas. FIG. 9B illustrates the gas distribution at different flow rates of gas. FIG. 9C illustrates the distribution of gas when using different positions of the apertures in the gas exchanger, and when the CF40 device contains liquid.

Figure 10:
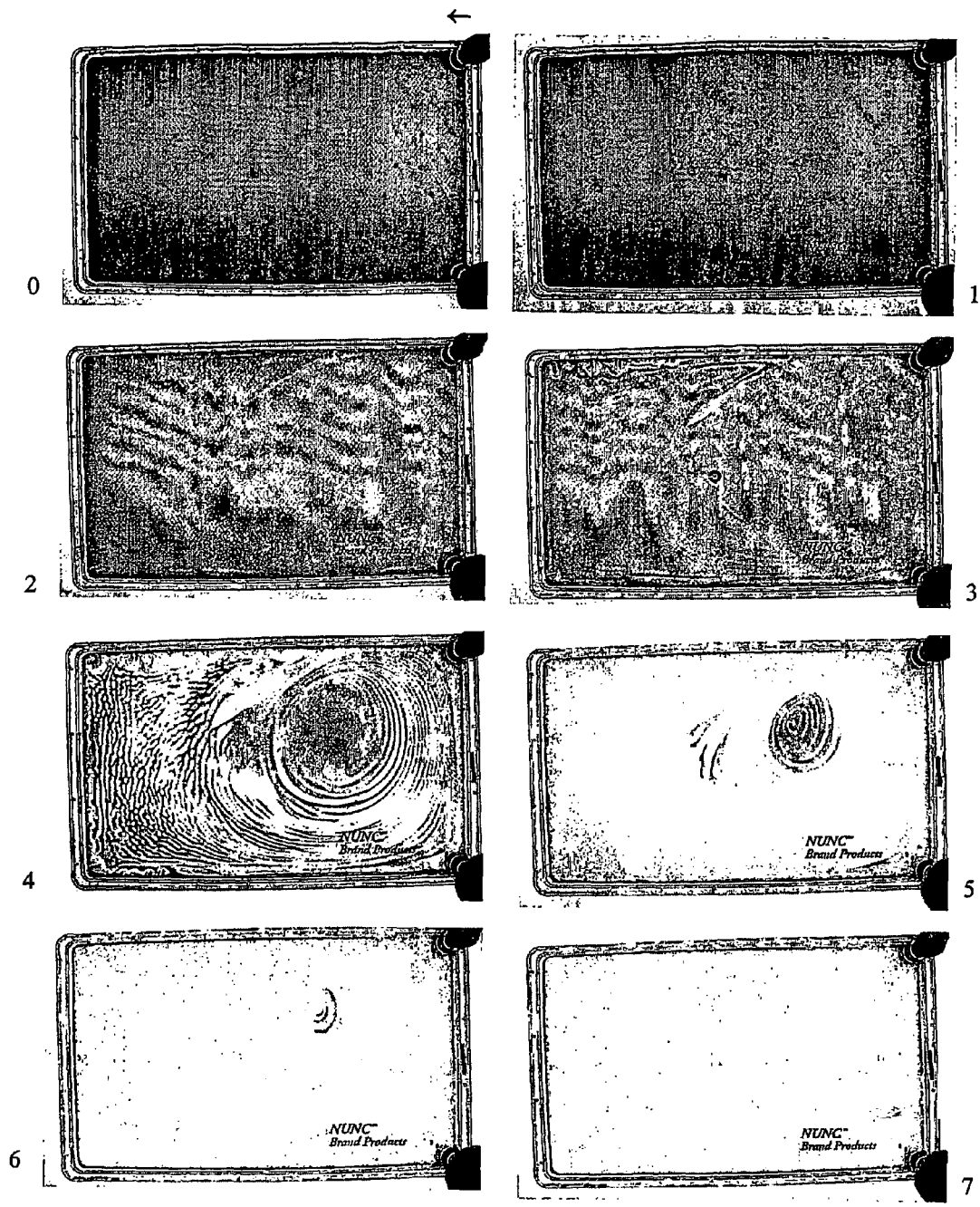
FIG. 10 illustrates aeration of one tray with a bicarbonate buffered medium comprising phenol red.
Figure 11A:
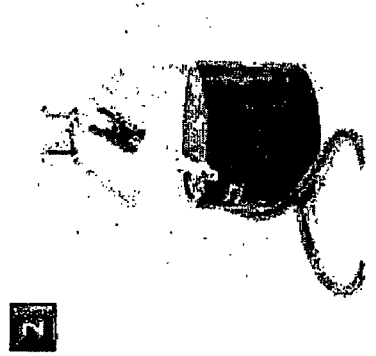
FIG. 11 illustrates how to operate a tray stack for cultivation of cells according to the invention.
Figure 11A:
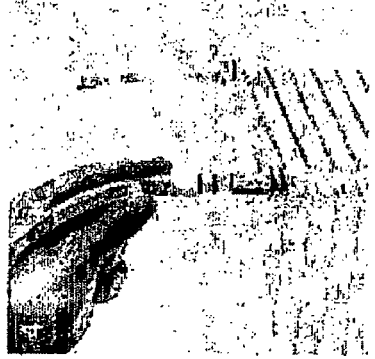
Figure 11A:
Figure 11A:
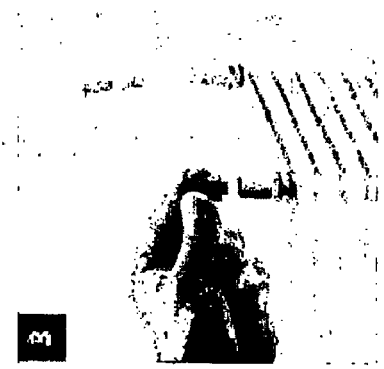
Figure 11D:
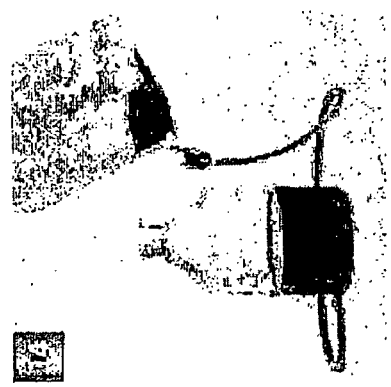
Figure 11D:
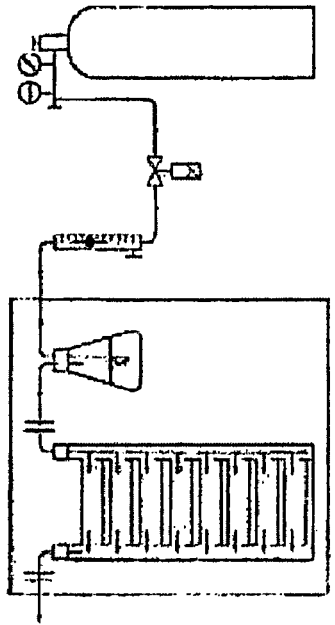
Figure 11D:
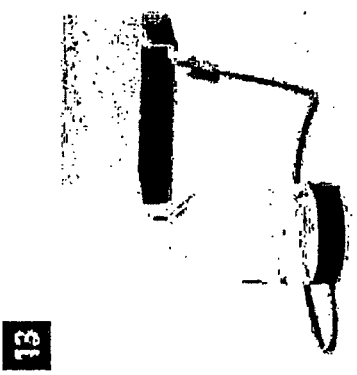
Figure 11D:
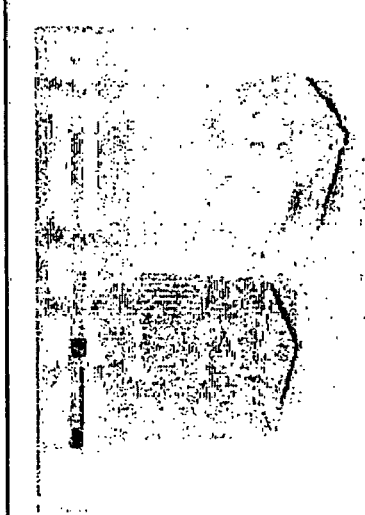

FIG. 10 shows the aeration of a bicarbonate buffered medium comprising phenol red.

The tray is gassed with $CO_2$ through a 0.4 mm aperture where the centre axis of the aperture points in the direction of the arrow.

FIG. 11 illustrates how to operate a tray stack for cultivation of cells according to the invention.

EXAMPLES

Example 1

Materials and Methods

A CF40 Forty Tray (Nunc, Roskilde) system with an $O_2$ sensor (Fiber-Optic Oxygen Minisensor from PreSens Precision Sensing GmbH, Germany) mounted into every third tray at the tray side opposing the connecting channels was used. The CF40 has a volume of approximately 36 L.

The initially atmospheric air-filled CF40 were gassed with $N_2$ under the conditions mentioned below and the relative oxygen percentage in the gas in the trays were determined after gassing with $N_2$ for 15 min, 30 min, 45 min and/or 60 min using a FIBOX Oxygen Meter from PreSens Precision Sensing GmbH, Germany.

Experiment 1A illustrates the time for distribution of a gas in the CF40 system. In the experiment is used a gas exchanger with 40 processed circular apertures having a diameter of 0.4 mm and wherein the centre axis of each aperture is extending into the respective tray opening in an angel of 45° to the tray sides. The flow rate of the supplied $N_2$ is 1.3 L/min and the oxygen percentages is determined after gassing with $N_2$ for 15 min, 30 min, 45 min and 60 min.

Experiment 1B illustrates the gas distribution at different flow rates of gas. In the experiment is used a gas exchanger positioned as described in Example 1A, and gas flow rates of 0.3 L/min, 1.3 L/min and 2.7 L/min. The oxygen percentage is determined after gassing for 30 min and 60 min.

Experiment 1C illustrates the distribution of gas in the trays of the CF40 system when using different gas exchanger designs: 1) a gas exchanger in the shape of a tube open in both ends, wherein the one end is placed at the bottom of the channel ("Bottom tube"), 2) a gas exchanger in the shape of a tube with 40 processed circular apertures, and wherein each aperture (0.4 mm internal diameter) is placed so that the centre axis of the aperture is extending into the respective tray opening in an angel of 45° to the tray sides ("Flute direct"), and 3) a gas exchanger in the form of a tube with 40 processed circular apertures (0.4 mm internal diameter), wherein the apertures are positioned opposite the respective tray openings, i.e. in such a way that gas flows through the apertures and out into the connecting channel in the opposite direction of the respective tray openings ("Flute indirect"). The flow rate of gas was 1.3 L/min and the relative oxygen percentage was determined after gassing with $N_2$ for 60 min.

Results and Discussion

The results shown in FIG. 8A shows that after gassing with $N_2$ for 60 minutes, the gas is distributed uniformly to trays 7 to 37.

These finding are supported by the result shown in FIG. 8B. This figure shows, that at a flow rate of 0.3 L/min the air in the lower half of the CF40 has not been exchanged even after 60 minutes, while a flow rate of 1.3 L/min gives a clearly better air exchange where about 80% of the air in the CF40 has been exchanged after 60 minutes, but it is still not sufficient to obtain a uniform gas exchange in the CF40 during that period. At a flow rate of 2.7 L/min about 90% of the gas in the CF40 has been exchanged after 30 minutes. Thus, it appears that the exchange rate of the CF40's approximately 36 L total air content can be more than doubled at a flow rate of 2.7 L/min as compared to 1.3 L/min.

FIG. 8C shows the correlation between the gas distribution and the design of the gas exchanger. By using a tube with one large aperture placed at the bottom of the first connecting channel, about 60% of the air is exchanged with $N_2$ in the trays in the upper half of the CF40 after 60 minutes. By using a tube with 40 processed circular apertures, wherein the apertures are positioned opposite the respective tray openings, i.e. in such a way that gas flows through the apertures and out into the connecting channel in the opposite direction of the respective tray openings, a gas exchange of 95% to 30% is obtained, the amount of gas exchanged decreases almost proportionally to the tray number.

The results in FIG. 8C show that that the distribution of gas in the CF40 system can also be considerably improved by using a gas exchanger in the shape of a tube wherein the apertures are positioned opposite the respective tray openings, i.e. in such a way that gas flows through the apertures and out into the connecting channel in the opposite direction of the respective tray openings ("flute indirect") or just by a tube with one large opening reaching to the bottom of the CF ("bottom tube"), as compared to just supplying gas to the connecting channel of the CF40, without the use of a gas exchanger. The results also show, that the "bottom tube" gas exchanger works best for a system with less than 25 trays.

Example 2

Materials and Methods

A CF40 Forty Tray (Nunc, Roskilde) system with an $O_2$ sensor (see Example 1) mounted into every third tray at the tray side opposing the connecting channels was used. The $O_2$ electrode is positioned in the headspace above the liquid, when 8 L liquid is applied to the device. The CF40 has a volume of approximately 36 L.

The initially atmospheric air-filled or 8 L liquid+atmospheric air-filled CF40 were gassed with $N_2$ under the conditions mentioned below and the relative oxygen percentage in the gas in the trays were determined after gassing with $N_2$ for 5 min, 20 min, 30 min and/or 60 min using the same apparatus as in Example 1.

Experiment 2A illustrates the time for distribution of a gas in the CF40 device. In the experiment is used a gas exchanger with 40 processed circular apertures (0.4 mm internal diameter), wherein the centre axis of each aperture extends along a longitudinal extension of the respective tray as illustrated in FIG. 7 (except that only one aperture is present per tray). The flow rate of the supplied $N_2$ is 2.7 L/min and the relative oxygen percentage is determined after gassing with $N_2$ for 5 min, 20 min, and 30 min.

Experiment 2B illustrates the gas distribution at different flow rates of gas. In the experiment is used a gas exchanger positioned as described in Experiment 2A, and gas flow rates of 1.0 L/min, 2.7 L/min and 8.7 L/min. The oxygen percentage is determined after gassing for 5 min, 30 min and 60 min.

Experiment 2C illustrates the distribution of gas in the CF40 device when using different positions of the apertures in the gas exchanger, and when the CF40 device contains liquid. Furthermore, the CF40 has been equipped with bacterial filters (allowing for a minimum flow rate of 2 L/min) and a humidifier to simulate cultivation conditions. In the experiment is used a gas exchanger as described in 2A and 2B ("Flute direct") without liquid in the device, and with 8 L liquid in the device ("Flute direct—with 8 L liquid"), and a gas exchanger wherein the apertures are displaced 2 mm to the tray opening ("Flute displaced 2 mm"). The flow rate of gas was 2.7 L/min and the relative oxygen percentage was determined after gassing with $N_2$ for 30 min Results and Discussion FIG. 9A shows that at a flow rate of $N_2$ of 2.7 L/min the gas is distributed uniformly between the 40 trays in the stacked, communicating tray device. The figure also shows, that 90% of the air in the device is exchanged with $N_2$ within 30 minutes.

FIG. 9B shows that the ventilation time period for obtaining a uniform distribution of gas in the trays in a 40-tray device depends on the flow rate of the gas supplied to the gas exchanger. At a flow rate of 1 L/min it takes at least 60 minutes before between 70% and 85% of the gas has been exchanged in the trays, i.e. the gas is not distributed uniformly in the trays. At a flow rate of 2.7 L/min 90% of the gas is exchanged within 30 minutes, while a gas flow of 8.7 L/min leads to an exchange of about 70% of the gas in 5 minutes. Thus, the flow rate of a gas supplied to a gas exchanger in a CF40 device should be at least 2 L/min or 50 ml/min per tray.

FIG. 9C shows that addition of a humidifier and bacterial filter to the CF40 device still gives a uniform gas exchange where about 80% of the air is replaced with $N_2$ after 30 minutes. Furthermore, at a flow rate of 2.7 L/min a displacement of the apertures in the gas exchanger in relation to the tray openings has only a minor influence on the uniformity of the gas distribution. The figure also illustrates a simulation of gas exchange under cultivation conditions, wherein 8 liters of liquid is added to the tray. The addition of liquid has no significant impact on the speed or uniformity of the gas exchange, but it is expected that the more liquid in the trays the less air and, accordingly, the faster exchange of gas.

As shown in FIGS. 8C and 9C, the distribution of gas in a tray stack according to the invention may be considerable improved, even if the aperture is positioned in such a way that gas flows through the aperture in question and out into the connecting channel at a distance from the corresponding opening of the respective tray, e.g. the gas flow out of the aperture takes place in the opposite direction of the tray opening (FIG. 8C), or is directed away from the tray opening, or, the aperture is displaced by, e.g., 2 mm relative to the tray opening (FIG. 9C).

Example 3

Materials and Methods

A CF1 Tray (Nunc, Roskilde) device with a tube with a 0.4 mm processed circular aperture, wherein the centre axis of the aperture points in the direction of the arrow was used. The tray contained 200 mL of a bicarbonate buffered medium comprising phenol red as a pH indicator.

The tray was gassed with $CO_2$ at a flow rate of 50 ml/min, and pictures were taken every minute through 7 minutes after start of gassing to illustrate the aeration of the medium in the tray.

Results and Discussion

FIG. 10 shows the aeration of the medium with $CO_2$, and thus the distribution of gas in the tray, which may also be deduced from the figure. The medium along the sides of the tray is aerated first, i.e. the gas stream is moving from the aperture along the sides of the tray all the way around the tray sides from the gas exchanger in the first connecting channel to the second connecting channel. This movement of gas is reflected in the colour changes of the medium.

From the figure it is also seen, that the supply of gas leads to a uniform distribution within a short ventilation time period caused by effective exchange of gas in the headspace above the liquid in the trays and stirring of the liquid by the gas flow.

The invention claimed is:

1. A tray stack for cultivation of cells in a liquid, comprising:
 a plurality of trays that are positioned on top of each other when the trays are in a horizontal position, and
 a first connecting channel, each tray having an opening through which the tray communicates with the first connecting channel, the channel having
 a gas exchanger having a first internal diameter and comprising at least one processed aperture in a sidewall of the gas exchanger, said processed aperture having a second internal diameter for distribution of gas to the trays, wherein the second internal diameter is in the range from about 0.4 mm to 2.0 mm, and the first internal diameter is greater than the second internal diameter, and
 when the tray stack is in use, the liquid is in direct contact with gas in the trays.

2. The tray stack according to claim 1, wherein the tray stack is made of material that withstands sterilization.

3. The tray stack according to claim 2, wherein the material is selected from a thermo-plastic material.

4. The tray stack according to claim 2, wherein the material can be sterilized by irradiation.

5. The tray stack according to claim 2, wherein the material melts by autoclaving.

6. The tray stack according to claim 3, wherein the material is selected from the group consisting of polyethylene, polypropylene, polystyrene, polycarbonate, polyurethane, polysulfone, polymethylpentene, polymethylmetacrylate, polyethyleneterepthtalate, polytetrafluoroethylene, and ABS (acrylonitrilbutadiene styrene).

7. The tray stack according to claim 1, wherein the gas exchanger has a plurality of processed apertures.

8. The tray stack according to claim 1, wherein the number of processed apertures of the gas exchanger equals the number of trays.

9. The tray stack according to claim 1, wherein the tray stack contains at least 10 trays.

10. The tray stack according to claim 1, wherein the tray stack contains at least 15 trays.

11. The tray stack according to claim 1, wherein the tray stack contains at least 20 trays.

12. The tray stack according to claim 1, wherein when in use flow rate of gas per tray during a time period for ventilation is within the range of about 50 ml/min to about 500 ml/min.

13. The tray stack according to claim 1, wherein when in use flow rate of gas per tray during a time period for ventilation is 50 ml/min, and the second internal diameter is 0.4 mm.

14. The tray stack according to claim 12, wherein a second flow rate of gas per tray during a second time period is at least 5 times greater than the flow rate during the time period for ventilation, and said second flow rate is sufficient to cause stirring of the liquid in the trays.

15. The tray stack according to claim 1, wherein each tray further has a second opening through which the tray communicates with a second connecting channel for exchange of fluid between the second connecting channel and the respective tray, the tray stack further comprising a sterile filter at an input opening to the first connecting channel.

16. A tray stack for cultivation of cells in a liquid, comprising:
   a plurality of trays that are positioned on top of each other when the trays are in a horizontal position, and
   a first connecting channel, each tray having an opening through which the tray communicates with the first connecting channel, the channel having
   a gas exchanger having a first internal diameter and comprising at least one processed aperture in a sidewall of the gas exchanger, said processed aperture having a second internal diameter for distribution of gas to the trays,
   wherein the first internal diameter is greater than the second internal diameter, and said processed aperture has an area within the range of about $0.125$ mm$^2$ to $3.5$ mm$^2$, and
   when the tray stack is in use, the liquid is in direct contact with gas in the trays.

* * * * *